United States Patent
Balachandran

(10) Patent No.: US 11,311,668 B2
(45) Date of Patent: Apr. 26, 2022

(54) AUTO-CALIBRATION OF PHYSIOLOGICAL RESPONSE ESTIMATES FOR CLOSED-LOOP INSULIN DELIVERY USING PATIENT-SELECTED STANDARDIZED MEALS

(71) Applicant: Verily Life Sciences LLC, South San Francisco, CA (US)

(72) Inventor: Ganesh Balachandran, Mountain View, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 704 days.

(21) Appl. No.: 15/810,649

(22) Filed: Nov. 13, 2017

(65) Prior Publication Data
US 2018/0169331 A1 Jun. 21, 2018

Related U.S. Application Data

(60) Provisional application No. 62/434,722, filed on Dec. 15, 2016.

(51) Int. Cl.
| | | |
|---|---|---|
| *G01N 33/48* | (2006.01) | |
| *G01N 31/00* | (2006.01) | |
| *A61M 5/172* | (2006.01) | |
| *G16H 50/50* | (2018.01) | |
| *A61B 5/00* | (2006.01) | |
| *G16H 50/20* | (2018.01) | |
| *G16H 20/17* | (2018.01) | |
| *A61B 5/145* | (2006.01) | |
| *A61M 5/142* | (2006.01) | |

(52) U.S. Cl.
CPC ....... *A61M 5/1723* (2013.01); *A61B 5/14532* (2013.01); *A61B 5/4839* (2013.01); *A61B 5/7275* (2013.01); *G16H 20/17* (2018.01); *G16H 50/20* (2018.01); *G16H 50/50* (2018.01); *A61M 5/142* (2013.01); *A61M 2205/50* (2013.01); *A61M 2205/502* (2013.01); *A61M 2205/505* (2013.01); *A61M 2205/52* (2013.01); *A61M 2205/6072* (2013.01); *A61M 2230/201* (2013.01); *A61M 2230/63* (2013.01)

(58) Field of Classification Search
None
See application file for complete search history.

(56) References Cited

U.S. PATENT DOCUMENTS

| | | | | |
|---|---|---|---|---|
| 2010/0030483 A1* | 2/2010 | Vering | ............... | A61B 5/14532 702/19 |
| 2010/0262434 A1* | 10/2010 | Shaya | .................. | A61B 5/7475 705/3 |
| 2011/0021898 A1* | 1/2011 | Wei | ......................... | G16H 50/20 600/365 |
| 2013/0041343 A1* | 2/2013 | Toumazou | .......... | A61M 5/1723 604/504 |
| 2014/0315162 A1* | 10/2014 | Ehrenkranz | ............ | G16H 20/60 434/127 |
| 2016/0166195 A1 | 6/2016 | Radecka et al. | | |
| 2016/0256087 A1* | 9/2016 | Doyle, III | .............. | G16H 20/60 |
| 2017/0216524 A1* | 8/2017 | Haider | ................ | A61M 5/1723 |

OTHER PUBLICATIONS

Hovorka, Roman. "Continuous glucose monitoring and closed-loop systems." Diabetic medicine 23.1 (2006): 1-12.*
Keith-Hynes, Patrick, et al. "The diabetes assistant: a smartphone-based system for real-time control of blood glucose." Electronics 3.4 (2014): 609-623.*
International Application No. PCT/US2017/065260, "International Search Report and Written Opinion", dated Mar. 22, 2018, 4 pages.
International Application No. PCT/US2017/065260, "International Preliminary Report on Patentability", dated Jun. 27, 2019, 4 pages.

* cited by examiner

*Primary Examiner* — Anna Skibinsky
(74) *Attorney, Agent, or Firm* — Kilpatrick Townsend & Stockton LLP

(57) ABSTRACT

Examples of determining and using physiological response estimates with glucose monitoring and insulin dosing systems and methods are disclosed. For example, one method includes receiving a selection of food items from a predefined catalog of food items as being part of a meal associated with a user profile, the catalog including nutritional information corresponding to food items in the catalog; determining nutritional information of the meal based on the nutritional information of each selected food item; receiving a notification from a user interface that a user associated with the user profile has started eating the meal; receiving successive indications of the user's glucose levels; computing a physiological response estimate associated with the user profile and the meal based on the successive indications of the user's glucose levels and the nutritional information of the meal.

28 Claims, 5 Drawing Sheets

AUTO-CALIBRATION OF PHYSIOLOGICAL RESPONSE ESTIMATES FOR CLOSED-LOOP INSULIN DELIVERY USING PATIENT-SELECTED STANDARDIZED MEALS

CROSS-REFERENCES TO RELATED APPLICATIONS

The present application is related to and claims the benefit of priority of U.S. Provisional Application No. 62/434,722, filed Dec. 15, 2016, titled "AUTO-CALIBRATION OF PHYSIOLOGICAL RESPONSE ESTIMATES FOR CLOSED-LOOP INSULIN DELIVERY USING PATIENT-SELECTED STANDARDIZED MEALS," the entirety of which is incorporated herein by reference.

TECHNICAL FIELD

The present disclosure relates generally to biosensors. More specifically, but not by way of limitation, this disclosure relates to determining and using physiological response estimates with glucose monitoring and insulin dosing systems and methods.

BACKGROUND

When a person eats food, her blood glucose level will begin to rise as her body digests the food and absorbs it into her blood stream. To regulate the amount of glucose in her blood, her pancreas will produce and release insulin, which causes her liver to begin absorbing and storing glucose as glycogen, causing her blood glucose level to drop, ultimately returning to a normal level. However, some people, referred to as diabetics, are less able or unable to produce sufficient insulin to properly regulate their blood glucose. As a result, diabetics will periodically administer insulin to maintain a normal blood glucose level. However, everyone has their own insulin sensitivity, which impacts how quickly they respond to administered insulin as well as how much of a response they have. Thus, to properly dose herself, a patient may determine her insulin sensitivity as well as other physiological response estimates. Improper dosing can lead to hyperglycemia or hypoglycemia, both of which can cause short and long-term health problems.

SUMMARY

Various examples are described for determining and using physiological response estimates with glucose monitoring and insulin dosing systems and methods. For example, one disclosed example method includes receiving, by a processing device, a selection of food items from a predefined catalog of food items as being part of a meal associated with a user profile, the catalog including nutritional information corresponding to food items in the catalog; determining, by the processing device, nutritional information for the meal based on the nutritional information of each selected food item; receiving, at the processing device, a notification from a user interface that a user associated with the user profile has started eating the meal; receiving, by the processing device from a continuous glucose monitor associated with the user profile, successive indications of the user's glucose levels; and computing a physiological response estimate associated with the user profile and the meal based on the successive indications of the user's glucose levels and the nutritional information of the meal.

One disclosed example non-transitory computer-readable medium in which instructions executable by a processing device are stored to cause the processing device to: receive a selection of a plurality of food items from a predefined catalog of food items as being part of a meal associated with a user profile, the catalog including nutritional information corresponding to food items in the catalog; determine nutritional information of the meal based on the nutritional information of each selected food item; determine changes in the glucose levels of a user associated with the user profile in response to the user eating the meal; and compute a physiological response estimate associated with the user profile and the meal based on the changes in the glucose levels and the nutritional information of the meal.

One disclosed example system includes a processing device and a memory device on which instructions are stored to cause the processing device to: receive a selection of a plurality of food items from a predefined catalog of food items as being part of a meal associated with a user profile, the catalog including nutritional information corresponding to food items in the catalog; determine nutritional information of the meal based on the nutritional information of each selected food item; and compute a physiological response estimate associated with the user profile and the meal based on changes in the user's glucose levels in response to the user eating the meal and the nutritional information of the meal.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
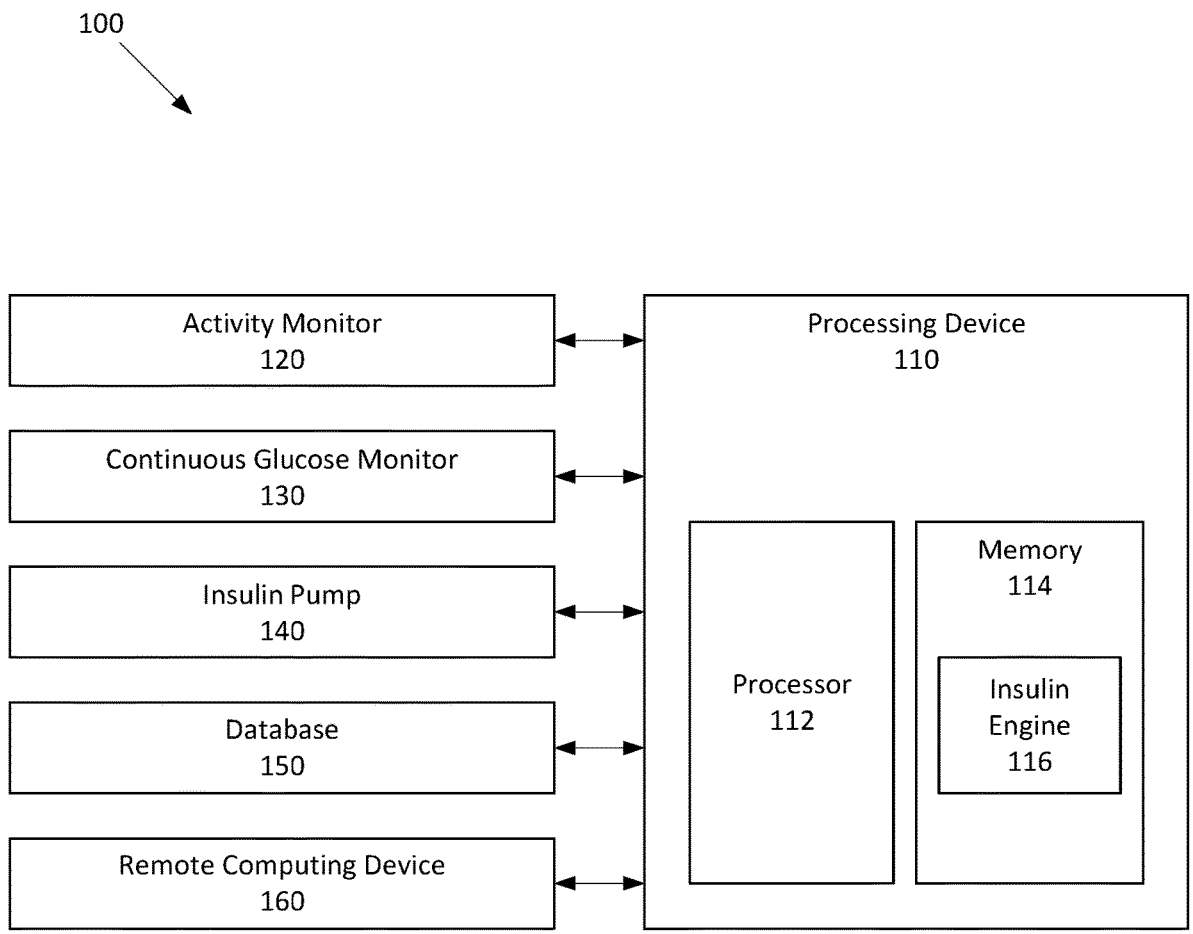
FIG. 1 is a block diagram of an example closed-loop glucose monitoring and insulin dosing system according to one example of the present disclosure.

Certain aspects and features relate to determining and using physiological response estimates with glucose monitoring and insulin dosing systems and methods. In one illustrative example, a person uses a continuous glucose monitor to monitor her glucose levels, and has an insulin pump to provide her with doses of insulin to help regulate her glucose level. However, because insulin dosing is based on the person's physiological response (e.g., insulin sensitivity or digestive rate), her physiological response may be computed based on a calibration process. A closed-loop insulin delivery system can use physiological response estimates determined by the calibration process to determine a proper insulin dosing for the person.

To determine her physiological response estimates, the person enters information about food she eats into her mobile device and uses her mobile device to receive measured glucose levels from a continuous glucose monitor ("CGM") that she wears. In this example, to enter the food she eats into her mobile device, she launches a glucose monitoring application and selects a meal from a catalog of meals available within the application, or she can enter individual food items that she is preparing to eat. After selecting a meal, or entering the specific food items, she presses a button on the mobile device to indicate that she is beginning to eat the meal.

The mobile device accesses information about the meal (or food items) from a database to obtain nutritional information about the food, such as glycemic indices, calories, etc. In addition, the mobile device receives successive glucose measurements from her CGM. Based on the information about the meal (or food items), and the measurements of her glucose levels over time, the mobile device determines her insulin sensitivity and other physiological estimates, which can include pathological estimates. In some examples, during a calibration process, an amount of insulin dispensed into the user is determined by the mobile device. The mobile device uses the amount of insulin, the nutritional information about the meal, and the measurements of her glucose levels to determine her insulin sensitivity. The mobile device then transmits the insulin sensitivity estimates to a cloud storage device, where it can be accessed by the user, her doctor, her insulin pump, etc. In some examples, the mobile device may also send a signal to the user's insulin pump to cause the insulin pump to output a quantity of insulin.

The example system described above can be referred to as a "closed-loop" system because it includes a feedback loop for obtaining the user's glucose levels and for providing doses of insulin based on those glucose levels, as well as other information, such as the user's determined insulin sensitivity estimates.

In some examples, a closed-loop glucose monitoring and insulin dosing system provides accurate and precise treatment for diabetics. The system continuously monitors changes in the user's blood glucose level and dispenses insulin into the user to keep a user's blood glucose level stable. The system determines an insulin dosing schedule based in part on the user's physiological response estimates (e.g., the user's insulin sensitivity or digestive rate), which can be determined or updated during a calibration process. A calibration process can be performed at predetermined intervals (e.g., once a week) or can be performed as part of every meal. During the calibration process, the system receives a selection of one or more food items that are part of a meal selected by the user. In some examples, the system receives the selection based on the user scanning an identifier (e.g., a barcode, QR code, or nutrition label) on a packaging of the food item. The system determines information about the meal (e.g., a glycemic index, a composition, or nutritional information about the meal) from a database of information on food items.

The system can monitor the changes in the user's glucose level in response to the user eating the meal. In some examples, the system determines the user's digestive rate by measuring a delay between receiving a notification that the user has begun eating the meal and an increase in the user's glucose level. A user's digestive rate may vary based on the type of meal. The digestive rate for a particular meal can be recorded and updated when the user eats the same meal again. In additional or alternative examples, the system measures a delay between the user receiving a dose of insulin and a reduction in the user's glucose level. The system determines the insulin sensitivity estimate for a user based in part on the delay, previously determined insulin sensitivity estimates, the user's digestive rate, information about the meal, activity level, information about current medications, and changes to the user's glucose level.

The system can provide more accurate insulin dosing schedules for a user than existing methods by determining a user's physiological response estimates more accurately and more frequently. In some examples, existing clinical testing is expensive (e.g., $20,000 per visit) and has limited availability (e.g., once a year). Examples of disclosed systems can be implemented with a closed-loop glucose monitoring and insulin dispensing system to update a user's physiological response based on data collected after every meal.

Existing clinical testing can involve the user fasting, spending 12-24 hours in a hospital, eating a predetermined meal (e.g., a glucose solution), and generally determining whether the user is either insulin sensitive or not. Examples of disclosed systems can determine a quantitative representation of the user's insulin sensitivity estimate based on user selected meals at the user's convenience.

In some examples, a user's insulin sensitivity estimate may change over time based on diet and exercise. Examples of disclosed systems can use continuous blood glucose data, user selected meals, and activity information to periodically update the recorded insulin sensitivity estimate and improve the accuracy of the user's insulin dosing schedule. Some disclosed systems can allow the user to select when and what to eat in order to update the user's insulin dosing schedule.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative aspects but, like the illustrative aspects, should not be used to limit the present disclosure.

FIG. 1 shows an example of a closed-loop glucose monitoring and insulin dosing system. The example system 100 shown in FIG. 1 includes a processing device 110 that is in communication with an activity monitor 120, a CGM 130, an insulin pump 140, a database 150, and a remote computing device 160. In this example processing device 110 receives information from the activity monitor 120 or the CGM 130, and uses that information to determine insulin dosing information to provide to the insulin pump to dispense insulin to a patient. The processing device 110 may obtain information from, or store information in, the database 150, such as physiological response estimates, and use such information in conjunction with the information from the activity monitor 120 or CGM 130 to determine the insulin dosing information. In some examples, the processing device 110 may provide physiological response estimates or insulin dosing information to the remote computing device 160, or it may receive such estimates or information from the remote computing device 160.

In some examples, the activity monitor 120, CGM 130, and insulin pump 140 are all worn by a user. The activity monitor 120 can be incorporated into a wearable device, such as a wristband, necklace, eyeglasses, etc. In other examples, the activity monitor 120 is incorporated into multifunction devices such as smartphones, music players, etc. that can be carried by the user. The activity monitor 120 can continuously measure activity data such as heart rate, steps taken, stairs climbed, etc. In other examples, the activity monitor 120 can receive activity data from user input such as a type of activity, duration of activity, etc.

The CGM 130 can be a patch attached to the user's skin for continuously monitoring the user's glucose level. In some examples, the CGM 130 includes a sensor positioned underneath a user's skin for measuring a user's glucose level in tissue fluid. The sensor can wirelessly communicate the measurements to the processing device 110, a dedicated device, or a multifunction device such as a mobile device.

The insulin pump 140 can be coupled to the user for dispensing an amount of insulin into the user. The insulin pump 140 can include a pump and insulin supply housed in a case that can be worn by the user. The case can be attached to the user's clothing (e.g., a waistband or a sock) or incorporated into a patch that can be attached to the user's skin.

Although FIG. 1 depicts the system 100 with an activity monitor, some systems use additional or alternative sensors. In some examples, a system includes a heart rate sensor for continuously monitoring the heart rate of a user. In additional or alternative examples, a system includes a blood oxygen sensor for continuously monitoring the blood oxygen level of a user. The processing device 110 stores the information measured by the additional or alternative sensors and uses the information to more accurately determine a user's physiological response estimates.

One or more components may be added, subtracted, or combined from the configuration of the system 100 shown in FIG. 1 without departing from the scope of the present disclosure. In some examples, the processing device 110 or the database 150 are included in another component such as the CGM 130 or the insulin pump 140. In additional or alternative examples, the processing device 110 is part of the remote computing device 160 or part of a remote device independent from the system 100. Performing processing (e.g., determining an insulin estimate) at a remote device may save processing power or battery life of user devices.

Each component of the system 100 can be communicatively coupled using any wireless communication protocol (e.g., WiFi or Bluetooth) or a wireline. In some examples, the CGM 130 is communicatively coupled directly to the insulin pump 140 such that the insulin pump 140 receives information about the user's glucose level directly from the CGM 130. In additional or alternative examples, the CGM 130 is communicatively coupled directly to the database 150 such that glucose level measurements are stored in the database 150 by the CGM 130. Routing information directly between components can save processing power and the battery life of the processing device 110. In some examples, the processing device 110, the activity monitor 120, the CGM 130, and the insulin pump 140 can be associated with a user profile. The user profile can be linked to a specific user.

The processing device 110 can include any number of processors 112 configured for executing program code stored in memory 114. Examples of the processing device 110 can include a microprocessor, an application-specific integrated circuit ("ASIC"), a field-programmable gate array ("FPGA"), or other suitable processor. In some examples, the processing device 110 is a dedicated processing device used for glucose monitoring and insulin dosing. In additional or alternative examples, the processing device 110 is a multifunction processing device. The processing device 110 can be part of a mobile device that includes a display and a user interface for receiving user inputs. The processing device 110 can process the user inputs and perform functions such as transmitting cellular data for determining physiological response estimates.

The processing device 110 can include (or be communicatively coupled with) a non-transitory computer-readable memory 114. The memory 114 can include one or more memory devices that can store program instructions. The program instruction can include for example, an insulin engine 116 that is executable by the processing device 110 to perform certain operations described herein.

The operations can include receiving a selection of a food item from a user. In some examples, the processing device 110 receives a signal from a mobile device indicating a selection of a Weight Watchers® meal and communicates with the database 150 to determine information (e.g., a glycemic index) of the meal. In additional or alternative examples, the meal can be any prepackaged meal. The processing device 110 may receive an identifier (e.g., a barcode) scanned by the mobile device. The processing device 110 can use the identifier to request the information about the meal from the database 150.

In some examples, the processing device 110 receives a selection of food items that are part of a meal. The user selects individual food items that make up the meal from a predetermined catalog of food items displayed to the user on a user interface. The predetermined catalog of food items can include any food item that has information about the food item stored in the database 150. The processing device 110 determines the information for each selected food item by accessing the database 150 and determines information about the meal based on the information for the food items.

In additional or alternative examples, the user selects a custom food item that is not present in the predetermined catalog of food items. The processing device 110 receives information about the custom food item from the user and transmits the information about the custom food item to the database 150. The database 150 stores the information such that the custom food item is added to the predetermined catalog and available to be selected by the user or other users.

The operations can further include determining an insulin sensitivity estimate for the user. For example, after receiving a selection of a meal or one or more food items, the device may receive an indication that the user has started eating. The notification can be a signal from a user interface or the processing device can determine the user has started eating after a predetermined delay from receiving the selection of the food item. The processing device 110 also receives signals from the CGM 130 indicating changes in the user's glucose level and the activity monitor 120 indicating activity information about the user. The processing device 110 may store the activity information and retrieves activity information from a predetermined period of time prior to the user starting the meal. The processing device 110 uses the activity information, the changes in glucose level, and the information about the meal to calculate an insulin sensitivity estimate for the user. In additional or alternative examples, the processing device 110 stores the insulin sensitivity estimate and may use past insulin sensitivity estimates to update any previously-determined insulin sensitivity estimate.

The operations can further include transmitting a signal based on the insulin sensitivity estimate. In some examples, the processing device transmits the signal to the database 150 for storing or updating the insulin sensitivity estimate. In additional or alternative examples, the processing device transmits the signal to the insulin pump 140. The signal may include an insulin dosing schedule determined by the processing device 110 or the remote computing device 160 based on the insulin sensitivity estimate. The pump dispenses an amount of insulin into the user based on the insulin dosing schedule and the user's glucose level.

Although FIG. 1 depicts the processing device 110, activity monitor 120, the CGM 130, the insulin pump 140, the database 150, and the remote computing device 160 as independent devices in the system 100, other implementations are possible. For example, an activity monitor can include a processing device, a CGM, an insulin pump, or any combination thereof. In additional or alternative examples, a CGM or an insulin pump can include any combination of the other components depicted in FIG. 1.

Figure 2:
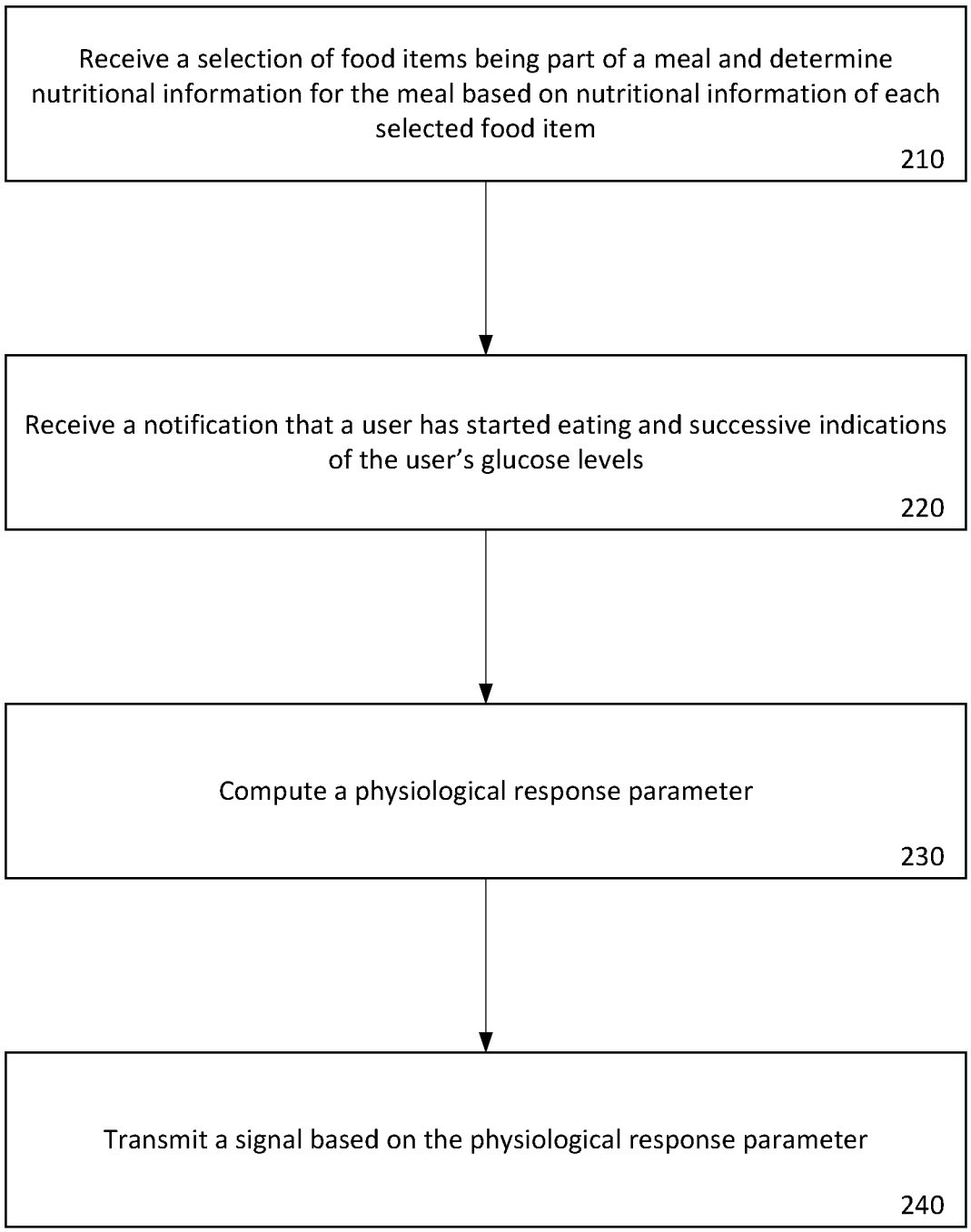
FIG. 2 is a flow chart of an example process for determining physiological response estimates using closed-loop glucose monitoring and insulin dosing systems and methods according to one example of the present disclosure.

FIG. 2 shows an example of a process for determining a physiological response estimate using a closed-loop glucose monitoring and insulin dosing system. The process is described with respect to the example system 100 shown in FIG. 1; however, the process is not limited to such a system. Instead, any suitable system according to this disclosure may be employed.

In block 210, the processing device 110 receives a selection of food items being part of a meal and determines a glycemic index for the meal based on a on a glycemic index of each selected food item. In this example, the processing device is included in a mobile phone, but could be other types of devices as discussed above with respect to FIG. 1. In this example, the user selects a Weight Watchers® meal by scanning an identifier (e.g., a barcode, QR code, or nutritional label) on the packaging of the meal with a camera on her mobile phone. The processing device 110 receives a signal from the camera identifying the selection of the meal. The processing device 110 accesses the database 150 and uses the identifier to locate information about the meal include a glycemic index for the meal.

In some examples, the meal can be a combination of food items from a predefined catalog of food items associated with a user profile, and the processing device 110 determines a glycemic index for a meal based on the glycemic indices of each of the selected food items. The processing device 110 can determine additional information about a meal including a composition of the meal and nutritional information of the meal. In some examples, the predefined catalog can include a list of food items or meals that have an associated glycemic index value stored in the database 150 or in memory 114. The predefined catalog may include prepackaged food (e.g., a boxed meal) having uniform composition and nutritional information.

In some examples, the processing device 110 displays the predefined catalog of food items to the user for selection. The user may then select one or more individual food items, which can be grouped by the processing device 110 to create a meal. After receiving the selection of the food items, the processing device 110 determines the glycemic index information for each of the selected food items. For example, the processing device 110 may access the database 150 to obtain the glycemic index information, or other nutritional information. In some examples, the processing device 110 may instead access nutritional information, including glycemic index information, by searching the internet for such information. In additional or alternative examples, the processing device 110 receives information (e.g., a glycemic index) associated with a custom meal from a user. For example, the user may input a name to be stored with the information in the database 150 for later selection by the user. The information stored to the database 150 can be publicly-available such that other users can access and select the custom meal. In some examples, the processing device 110 stores information about a set of meals locally in memory 114 for quicker and private access.

In block 220, the processing device 110 receives a notification that the user has started eating the meal, and begins receiving successive indications of the user's glucose levels from the CGM 130. In this example, the processing device 110 receives the notification from a user interface in response to the user pressing a button. The user may press a button on the user instructing the user interface to transmit the message after a predetermined period of time (e.g., 1 hour). In additional or alternative examples, the processing device 110 provides the notification based on determining the user has started eating. The processing device 110 may determine the user has started eating based on a predetermined period of time passing since the user selected the meal or based on a change in the user's glucose level.

In some examples, the processing device 110 receives real-time measurements of the user's glucose level from the CGM 130. The processing device analyzes the measurements and stores a record of information based on the measurements to the database 150. In additional or alternative examples, the processing device 110 may transmit a signal to the CGM 130 and request measurements for a period of time based on the time the user started eating the meal.

In block 230, the processing device 110 determines a physiological response estimate. In this example, the processing device 110 determines the insulin sensitivity estimate based on changes to the glucose level of the user in response to the user eating the meal. As the meal is digested by the user, glucose in the food items is absorbed into the user's bloodstream causing the user's blood glucose level to rise. The processing device measures changes in the user's glucose level and determines the user's insulin sensitivity estimate by comparing the changes in the user's glucose level to expected changes for an average non-diabetic.

In some examples, the expected changes are representative of expected changes for an average diabetic. The average diabetic can be based on a set of diabetics having the same type of diabetes as the user. In additional or alternative examples, the expected changes can be based on previous measurements of the user's glucose level. The processing device 110 requests previous measurements from the database 150. The processing device 110 can request the previous measurements include glucose levels measured after the user ate a meal with a glycemic index within a predetermined range (e.g., within 10 g of the meal presently eaten by the user).

In additional or alternative examples, the processing device 110 calculates a rate at which the user's glucose level changes per unit of insulin dispensed into the user. The insulin sensitivity estimate can be determined by comparing the changes in a user's glucose level to historical data illustrating how different insulin sensitivity estimates affect changes in glucose levels. One example process for determining a person's insulin sensitivity is described below with respect to FIG. 3.

In block 240, the processing device 110 transmits a signal based on the physiological response estimate. In this example, the processing device 110 transmits the signal to the insulin pump 140 to cause the insulin pump 140 to dispense a quantity of insulin into the user. The processing device 110 determines the amount of insulin to be dispensed based on the insulin sensitivity estimate of the user and the user's glucose level. Then the processing device 110 transmits the signal, including instructions to dispense the amount of insulin into the user, to the insulin pump 140.

In additional or alternative examples, the signal includes an insulin dosing schedule based on the insulin sensitivity estimate. The insulin dosing schedule can be a table describing an amount of insulin to be dispensed into the user given different glucose levels or rates of change of glucose levels. The insulin pump 140 can receive the user's glucose level directly from the CGM 130 and determine an amount of insulin to dispense into the user based on the insulin dosing schedule. The processing device 110 may determine the insulin dosing schedule based on the insulin sensitivity estimate or the processing device 110 can transmit the signal to the remote computing device 160. Determining the insulin dosing schedule at the remote computing device may save processing power or battery life of the processing device 110.

In additional or alternative examples, the signal is transmitted to a storage device (e.g., memory 114 or database 150) such that the insulin sensitivity estimate can be tracked or updated. Tracking a user's past insulin sensitivity estimates can allow the processing device 110 to more accurately determine the user's current insulin sensitivity estimate. The processing device 110 can also monitor changes in the user's insulin sensitivity and alert the user to changes in their health based on the changes. In additional or alternative examples, the signal is transmitted to a display for informing the user of the user's insulin sensitivity estimate. The user can use the information about their insulin sensitivity estimate to make decisions about their diet, activity, or medication.

Figure 3:
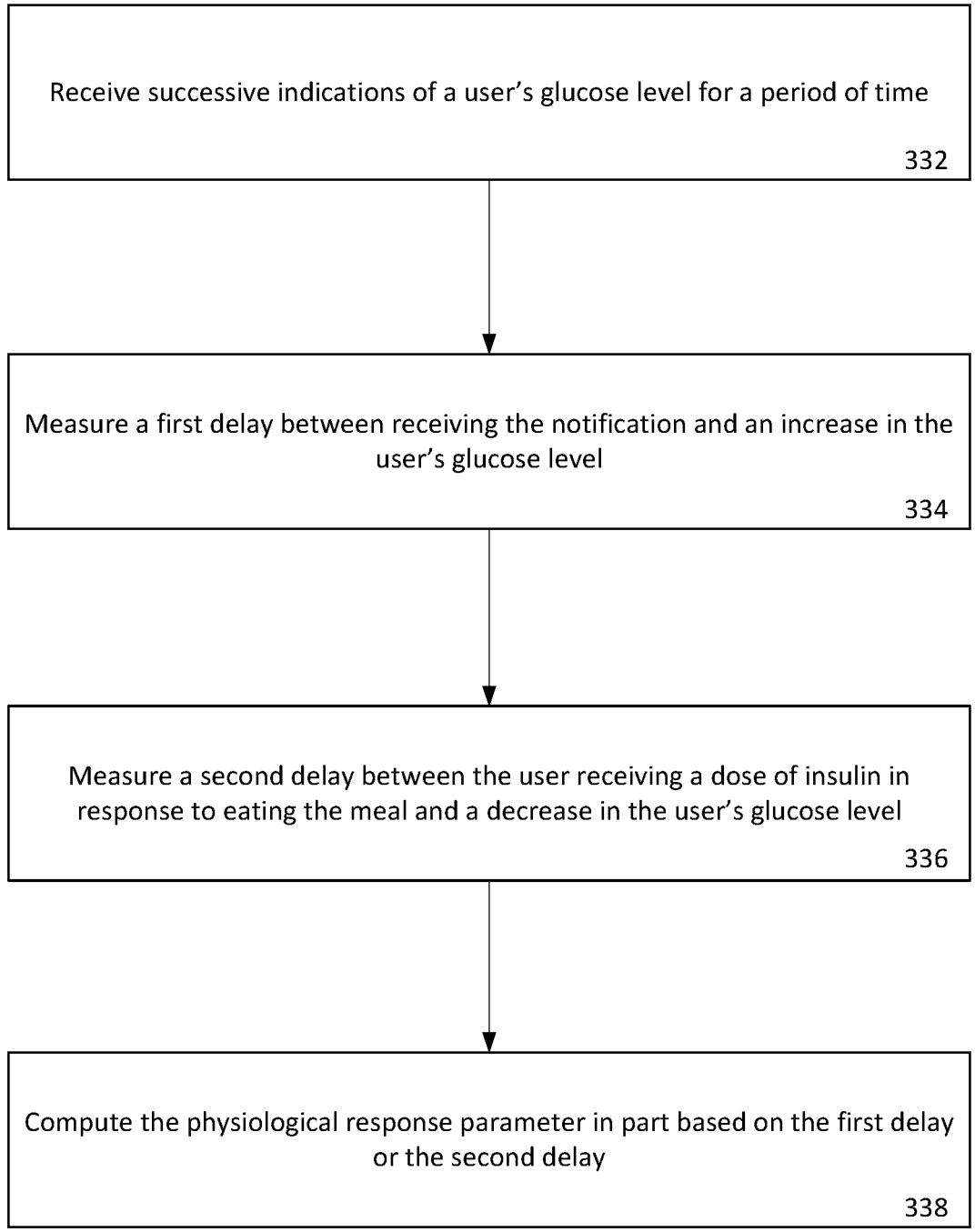
FIG. 3 is a flow chart of an example process for determining a physiological response estimate based on changes in a patient's glucose level according to one example of the present disclosure.

FIG. 3 is a flow chart of an example of a process for determining the physiological response estimate. Determining an accurate physiological response estimate can improve the treatment of individuals with diabetes. For example, accurately determining the insulin sensitivity estimate for a diabetic can prevent hyperglycemia or hypoglycemia by preventing the insulin pump 140 from dispensing too much or too little insulin into a user. The process of FIG. 3 will be discussed with respect to the system 100 shown in FIG. 1; however, as discussed above, any suitable system according to this disclosure may be employed.

In block 332, the processing device 110 receives successive indications of the user's glucose level for a period of time. In this example, the processing device 110 receives successive indications of the user's glucose level for one hour. During the hour, the processing device 110 received information to determine the user's insulin sensitivity estimate. In this example, the information includes a first delay between receiving the notification that the user started eating and an increase in the user's glucose level as well as a second delay between the user receiving a dose of insulin in response to eating the meal and a decrease in the user's glucose level. Sufficient information for determining the user's insulin sensitivity estimate can depend on the amount of prior information (e.g., previous insulin sensitivity estimates) available to the processing device 110.

In additional or alternative examples, the period of time is a period until the user's glucose level falls below a threshold value. The threshold value can be a resting glucose level for the user such that falling below the threshold value indicates the user's glucose level is no longer impacted by having eaten the meal. The processing device 110 may detect the period of time has elapsed and transmit a signal to the CGM 130 to stop transmitting glucose level information. The CGM 130 may detect the period of time has elapsed and cease transmission of glucose levels or reduce the frequency of transmitting glucose levels to the processing device 110.

In block 334, the processing device 110 measures a first delay between receiving the notification and an increase in the user's glucose level. In this example, the processing device 110 uses the delay to determine the user's digestive rate for the meal. The processing device 110 starts a timer in response to receiving the notification and stops the timer in response to detecting the increase in the user's glucose level. Determining the user's digestive rate can be further based on an amount of time the user's glucose level remains elevated as a result of the meal or a rate of increase of the user's glucose level as a result of the meal. In additional or alternative examples, the notification includes the start time, which the processing device 110 stores for use with another time recorded in response to the increase in the user's glucose level.

In block 336, the processing device 110 measures a second delay between the user receiving a dose of insulin in response to eating the meal and a decrease in the user's glucose level. In this example, the insulin pump 140 dispenses an amount of insulin based on an insulin dosing schedule as a part of the closed-loop system's response to an increase in the user's glucose level. The processing device 110 receives a signal from the insulin pump 140 to start the timer in response to the insulin pump 140 dispensing the amount of insulin. The processing device 110 further receives a signal from the CGM 130 to stop the timer in response to the CGM detecting a decrease in user's glucose level in response to the insulin. In additional or alternative examples, the processing device 110 instructs a predetermined amount of insulin to be dispensed by the insulin pump 140.

In additional or alternative examples, the processing device 110 measures the second delay between the user receiving a dose of insulin that is naturally produced by the user's pancreas and a decrease in the user's glucose level. The processing device 110 is communicatively coupled to a sensor for determining insulin dispensed by the user's pancreas. The sensor can be included in the CGM 130 and can transmit a start time to the processing device 110 in response to detecting a change in the user's glucose level that is not due to insulin dispensed by the insulin pump 140. The processing device 110 further receives measurements from the CGM 130 indicating the user's glucose level and the processing device 110 determines a stop time based on a decrease in the user's glucose level. The second delay is determined by taking the different in the start time and the stop time.

In block 338, the processing device 110 determines the physiological response estimate in part based on the first delay or second delay. In this example, the processing device 110 analyzes the first delay to determine a digestive rate. The processing device 110 uses the glycemic index of the meal eaten by the user and the user's digestive rate to determine a rate at which glucose is being absorbed into the user's blood stream. The processing device 110 uses the rate of glucose absorption to determine a model of expected changes in the user's glucose level without the introduction of insulin. The processing device 110 compares the model of expected changes with the measured changes in the user's glucose level after the introduction of insulin to determine the insulin sensitivity estimate.

In additional or alternative examples, the processing device 110 adjusts the model of expected changes in the user's glucose level based on the second delay. Adjusting the model of expected changes based on the second delay can provide a more accurate model by accounting for the user's delay in responding to the dose of insulin. The processing device 110 can compare the adjusted model of expected changes with the measured changes in the user's glucose level to determine the insulin sensitivity estimate.

Figure 4:
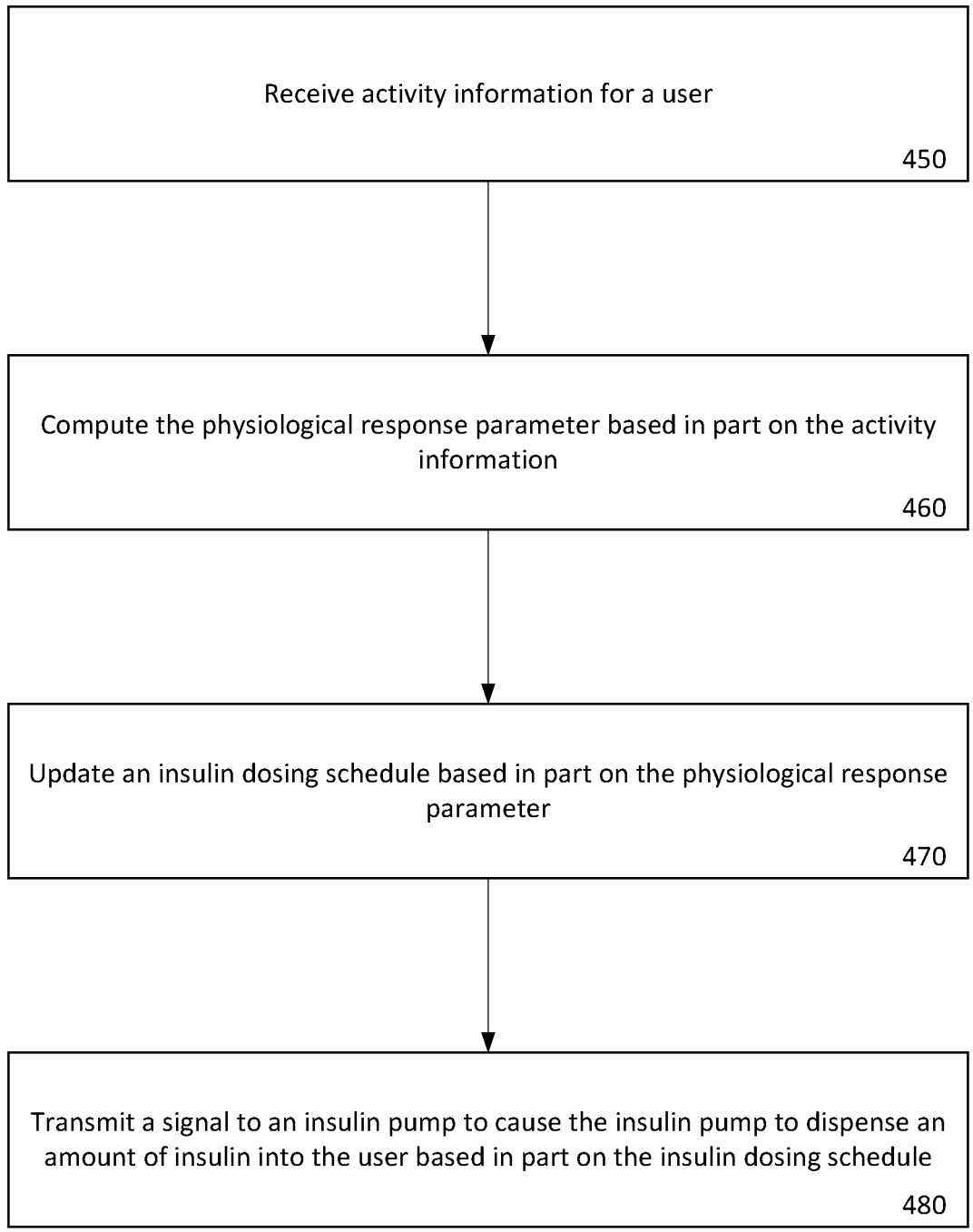
FIG. 4 is a flow chart of an example process for transmitting a signal to cause an insulin pump to dispense an amount of insulin based on an insulin dosing schedule according to one example of the present disclosure.

FIG. 4 is a flow chart of an example of a process for transmitting a signal to cause an insulin pump 140 to dispense an amount of insulin based on an insulin dosing schedule. The insulin dosing schedule can be a table associating the user's glucose level with a dosage of insulin that will reduce the user's glucose level to within a range of glucose levels. The process is described in terms of the system 100 in FIG. 1 but various systems could perform the process.

In block 450, the processing device 110 receives activity information for a user. In this example, the processing device 110 is included in a mobile device that includes a user interface for allowing the user to input activity information. The processing device 110 receives activity information from the user indicating a type of activity and a duration of an activity performed by the user. The processing device 110 stores the activity information in a portion of the memory 114 related to the user's recent activity.

In additional or alternative examples, the processing device 110 receives the activity information from the activity monitor 120. The activity monitor can be a wearable device or included in a multifunction device (e.g., a mobile phone) that measures activity. The activity information can include a time of the activity, a heart rate during the activity, or a duration of the activity. The processing device 110 can transmit the activity information to the database 150.

In block 460, the processing device 110 determines the physiological response estimate based in part on the activity information. Exercise can temporarily impact a user's physiological response estimate. For example, aerobic exercise within the 24 hours prior to a meal can increase a user's insulin sensitivity estimate. In this example, the processing device 110 determines a baseline insulin sensitivity for the user and determines an adjusted insulin sensitivity for the user based on the user's recent activity information. The processing device 110 stores the user's baseline insulin sensitivity estimate in the database 150 separate from the user's adjusted insulin sensitivity estimate. The processing device 110 uses the adjusted insulin sensitivity estimate to determine an insulin dosing schedule and to instruct the insulin pump 140 about an amount of insulin to dispense into the user. After a predetermined period of time, the processing device 110 updates the user's adjusted insulin sensitivity estimate in response to the user's previous activity information no longer affecting the user's insulin sensitivity. The processing device 110 may update the adjusted insulin sensitivity estimate based on recent activity information and the baseline insulin sensitivity estimate.

In block 470, the processing device 110 updates an insulin dosing schedule based in part on the physiological response estimate. In this example, the processing device 110 uses the user's adjusted insulin sensitivity estimate to update the insulin dosing schedule. The insulin dosing schedule can be a table stored in the memory 114 or on a memory included in the insulin pump 140. The insulin dosing schedule can also be stored in the database 150. The table can be used to look up insulin dosages based on the user's glucose level. The processing device 110 calculates an amount of insulin that will reduce the user's glucose level to within a predetermined range for each of a series of potential glucose levels. The amounts are based on the user's current insulin sensitivity estimate, which indicates how the user's glucose level will respond to an amount of insulin. After a predetermined amount of time, the insulin dosing schedule may be updated in response to the user's activity information no longer affecting the user's insulin sensitivity estimates.

In additional or alternative examples, the processing device 110 sues the user's baseline insulin sensitivity estimate to update the insulin dosing schedule. The insulin dosing schedule can be used to look up insulin dosages based on the user's glucose level and the user's recent activity level. The insulin dosing schedule can account for additional body estimates such as a user's digestive rate.

In block 480, the processing device 110 transmits a signal to an insulin pump 140 to cause the insulin pump 140 to dispense an amount of insulin into the user based in part on the insulin dosing schedule. In this example, the processing device 110 transmits the signal including the amount of insulin for the insulin pump 140 to dispense into the user. The processing device 110 determines the amount of insulin based on receiving the user's glucose level from the CGM 130 and applying the user's glucose level to the insulin dosing schedule. In additional or alternative examples, the signal includes the insulin dosing schedule and the insulin pump 140 uses the insulin dosing schedule and a measurement of the user's glucose level from the CGM 130 to determine the amount of insulin to dispense into the user.

Figure 5:
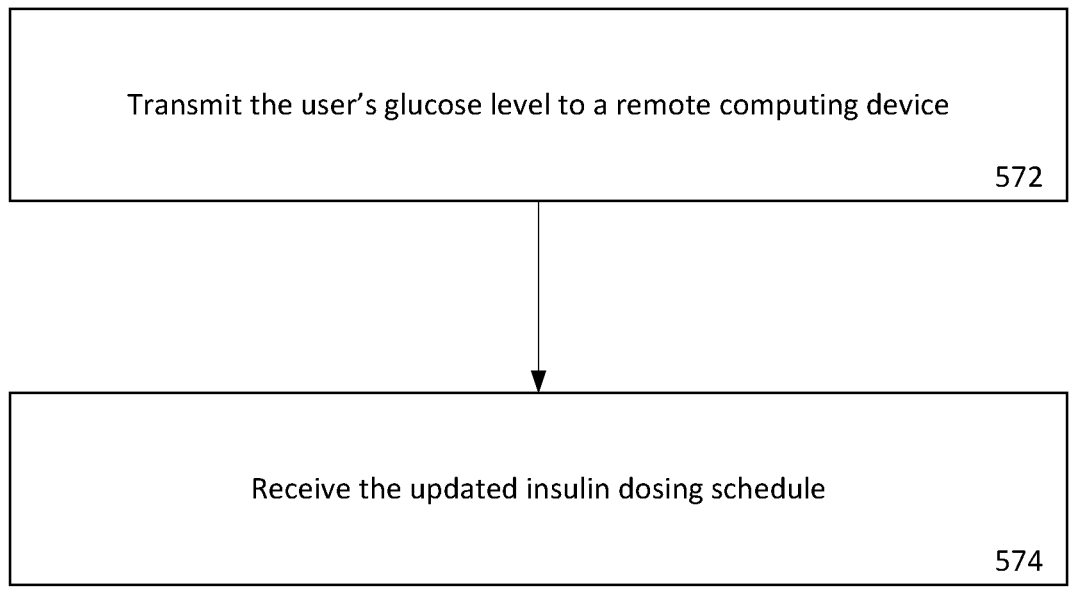
FIG. 5 is a flow chart of an example process for updating an insulin dosing schedule according to one example of the present disclosure.

FIG. 5 is a flow chart of an example of the process for updating an insulin dosing schedule as in block 470 in FIG. 4. The process is performed by the processing device 110, the remote computing device 160, or any other suitable device. In some examples, it may save processing power or battery life at the processing device 110 by updating an insulin dosing schedule at the remote computing device 160.

In block 572, the processing device 110 transmits the user's glucose levels to the remote computing device 160. In this example, the processing device 110 received the user's glucose levels from the CGM 130 in response to the user starting to eat a meal. The remote computing device 160 is communicatively coupled to database 150 and other databases that include models of glucose level responses based on different insulin sensitivity estimates. The remote computing device can access medical records and data (e.g., the user's insulin sensitivity estimates, other physiological response estimates, and information on the meal eaten by the user) for the user from database 150 and the other databases. The remote computing device 160 determines an insulin dosing schedule for the user based on the user's glucose levels and the information available from database 150 and the other databases. In additional or alternative examples, the processing device 110 transmits additional information including previous insulin sensitivity estimates, meal information, or other physiological estimates to the remote computing device 160. The remote computing device 160 determines an insulin dosing schedule for the user as discussed above with respect to FIG. 4, and transmits the insulin dosing schedule to the processing device 110.

In block 574, the processing device 110 receives the updated insulin dosing schedule from the remote computing device 160. In some examples, the processing device 110 is included in the insulin pump 140, which receive the updated insulin dosing schedule from the remote computing device 160. The insulin dosing schedule is used by the insulin pump 140 to dispense an accurate amount of insulin for maintaining a stable glucose level of the user. In additional or alternative examples, the processing device 110 is included in the CGM 130, which receives the updated insulin dosing schedule from the remote computing device 160. The CGM 130 can monitor changes in the user's glucose level and transmit signals to the insulin pump 140 to dispense an amount of insulin based on applying the measured glucose level to the insulin dosing schedule.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. The phrase "based on" should be understood to be open-ended, and not limiting in any way, and is intended to be interpreted or otherwise read as "based at least in part on," where appropriate. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present. Additionally, conjunctive language such as the phrase "at least one of X, Y, and Z," unless specifically stated otherwise, should also be understood to mean X, Y, Z, or any combination thereof, including "X, Y, and/or Z."

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A method comprising:
receiving, by a processing device, a selection of a plurality of food items from a predefined catalog of food items as being part of a meal associated with a user profile, the catalog comprising nutritional information corresponding to food items in the catalog;
determining, by the processing device, nutritional information for the meal based on the nutritional information of each selected food item;
receiving, at the processing device, a user input, via a user interface, providing a notification that a user associated with the user profile has started eating the meal;
receiving, by the processing device from a continuous glucose monitor associated with the user profile, a plurality of successive indications of a user's glucose levels, wherein at least a subset of the successive indications are received in response to receiving the notification and while the user eats the meal;
receiving, by the processing device, activity information from an activity monitor worn by the user, the activity information indicating an activity level of the user;
determining a physiological response estimate associated with the user profile and the meal based on (i) the successive indications of the user's glucose levels, including the subset of the successive indications, (ii) the nutritional information of the meal, and (iii) the activity level;
updating an insulin dosing schedule based at least in part on the physiological response estimate; and
transmitting, by the processing device, a signal based on the updated insulin dosing schedule to cause an insulin pump associated with the user profile to dispense an amount of insulin into the user based on the updated insulin dosing schedule.

2. The method of claim 1, further comprising determining, by the processing device, changes in the glucose levels based on the successive indications of the user's glucose levels, wherein computing the physiological response estimate is performed by the processing device and based at least in part on the changes in the glucose levels, wherein updating the insulin dosing schedule is performed by the processing device.

3. The method of claim 2, further comprising:
measuring, by the processing device, a delay between the notification and an increase in the user's glucose levels as indicated by the determined changes,
wherein computing the physiological response estimate is further based on the measured delay.

4. The method of claim 1, further comprising:
transmitting, by the processing device, the user's glucose levels to a remote computing device; and
receiving, by the processing device from the remote computing device, the updated insulin dosing schedule.

5. The method of claim 1, wherein determining the nutritional information for the meal comprises:
determining a glycemic index and a carbohydrates value of the meal,
wherein computing the physiological response estimate is further based on the glycemic index and the carbohydrates value of the meal.

6. The method of claim 1, further comprising:
determining, by the processing device, an amount of a dose of insulin dispensed into the user in response the notification; and measuring, by the processing device, a delay between the user receiving the dose of insulin and a decrease in the user's glucose levels,
wherein computing the physiological response estimate is further based on the measured delay and the amount of the dose of insulin.

7. The method of claim 1, wherein receiving the successive indications of the user's glucose levels comprises:
receiving the successive indications for a period of time after the notification; and
causing the continuous glucose monitor to cease transmitting indications after the period of time ends,
wherein the period of time ends after a predetermined time or when the user's glucose levels reaches a predetermined level.

8. The method of claim 1, wherein receiving the selection of the food item comprises:
receiving information from an identifier on a packaging of the food item by scanning a bar code, a QR code, a nutrition label, or any combination thereof; and
obtaining the nutritional information from a database of compositions of food items using the information.

9. The method of claim 1, wherein receiving the notification that the user associated with the user profile has started eating the meal comprises receiving the notification prior to receiving the selection of the plurality of food items.

10. A non-transitory computer-readable medium in which instructions executable by a processing device are stored for causing the processing device to:
receive a selection of a plurality of food items from a predefined catalog of food items as being part of a meal associated with a user profile, the catalog comprising nutritional information corresponding to food items in the catalog;
determine nutritional information of the meal based on the nutritional information of each selected food item;
receive a user input, via a user interface, providing a notification that a user associated with the user profile has started eating the meal;
receive, from a continuous glucose monitor associated with the user profile, a plurality of successive indications of a user's glucose levels, wherein at least a subset of the successive indications are received in response to receiving the notification and while the user eats the meal;
determine changes in glucose levels of a user associated with the user profile in response to the user eating the meal based on the successive indications of the user's glucose levels, including the subset of the successive indications;
receive activity information from an activity monitor worn by the user, the activity information indicating an activity level of the user;
determine a physiological response estimate associated with the user profile and the meal based on (i) the changes in the glucose levels, (ii) the nutritional information of the meal, and (iii) the activity level;
update an insulin dosing schedule based at least in part on the physiological response estimate; and
transmit a signal to an insulin pump associated with the user profile based on the updated insulin dosing schedule to cause the insulin pump to dispense an amount of insulin into the user.

11. The non-transitory computer-readable medium of claim 10, wherein the instructions are further executable by the processing device for causing the processing device to receive a notification from a user interface that the user started eating the meal.

12. The non-transitory computer-readable medium of claim 11, wherein the instructions to cause the processing device to receive the selection of the plurality of food items comprise instructions to cause the processing device to listen for the selection in response to receiving the notification.

13. The non-transitory computer-readable medium of claim 10, wherein the instructions are further executable by the processing device for causing the processing device to receive, from a continuous glucose monitor associated with the user profile, successive indications of the user's glucose levels, wherein the instructions to cause the processing device to cause the processing device to determine the changes in the glucose levels comprise instructions to cause the processing device to determine the changes based on the successive indications of the user's glucose levels.

14. The non-transitory computer-readable medium of claim 10, wherein the instructions are further executable by the processing device for causing the processing device to receive, from a remote computing device associated with the user profile, the changes in the glucose levels and the updated insulin dosing schedule.

15. The non-transitory computer-readable medium of claim 10, wherein the instructions are further executable by the processing device for causing the processing device to:
determine a glycemic index or a carbohydrates value of the meal,
wherein the instructions to cause the processing device to compute the physiological response estimate is further based on the glycemic index or the carbohydrates value of the meal.

16. The non-transitory computer-readable medium of claim 10, wherein the instructions are further executable by the processing device for causing the processing device to:
determine an amount of a dose of insulin dispensed into the user in response to the user eating the food,
wherein the instructions to cause the processing device to compute the physiological response estimate comprise instructions to cause the processing device to determine the physiological response estimate based on the amount of the dose of insulin.

17. The non-transitory computer-readable medium of claim 10, wherein the instructions are further executable by the processing device for causing the processing device to:
measure a delay between the user receiving a dose of insulin and a decrease in the user's glucose levels; and
wherein the instructions to cause the processing device to compute the physiological response estimate comprise instructions to cause the processing device to determine the physiological response estimate based on the delay.

18. The non-transitory computer-readable medium of claim 10, wherein the instructions to cause the processing device to receive the selection of the food item comprises instructions to cause the processing device to:
scan an identifier on a packaging of the food item;
receive information from the identifier; and
obtain the nutritional information from a database of compositions of food items using the information.

19. A system comprising:
a processing device; and
a memory device on which instructions are stored for causing the processing device to:
receive a selection of a plurality of food items from a predefined catalog of food items as being part of a meal associated with a user profile, the catalog comprising nutritional information corresponding to food items in the catalog;

determine nutritional information of the meal based on the nutritional information of each selected food item;

receive a user input, via a user interface, providing a notification that a user associated with the user profile has started eating the meal;

receive, from a continuous glucose monitor associated with the user profile, a plurality of successive indications of a user's glucose levels, wherein at least a subset of the successive indications are received in response to receiving the notification and while the user eats the meal;

receive activity information from an activity monitor worn by the user, the activity information indicating an activity level of the user;

determine a physiological response estimate associated with the user profile and the meal based on (i) changes in a user's glucose levels based on the successive indications of the user's glucose levels, including the subset of the successive indications, (ii) the nutritional information of the meal, and (iii) the activity level;

update an insulin dosing schedule based at least in part on the physiological response estimate; and transmit a signal to an insulin pump associated with the user profile based on the updated insulin dosing schedule to cause the insulin pump to dispense an amount of insulin into the user.

20. The system of claim 19, further comprising a continuous glucose monitor associated with the user profile to transmit successive indications of the user's glucose levels to the processing device.

21. The system of claim 20, wherein the processing device further comprises the continuous glucose monitor.

22. The system of claim 19, further comprising an insulin pump in communication with the processing device to receive signals from the processing device and dispense insulin based on the received signals.

23. The system of claim 19, further comprising a remote computing device communicatively coupled to the processing device, wherein the instructions are further for causing the processing device to:

transmit the user's glucose levels to the remote computing device; and receive, from the remote computing device, the updated insulin dosing schedule.

24. The system of claim 22, wherein the insulin pump comprises a continuous glucose monitor for measuring the user's glucose levels.

25. The system of claim 19, wherein the instructions are further for causing the processing device to:

determine a glycemic index and a carbohydrates value of the meal, wherein causing the processing device to determine the physiological response estimate is further based on the glycemic index and the carbohydrates value of the meal.

26. The system of claim 19, further comprising the activity monitor communicatively coupled to the processing device.

27. The system of claim 26, wherein the activity monitor comprises the processing device, a continuous glucose monitor, an insulin pump, or any combination thereof.

28. The system of claim 19, wherein the memory device further comprises instructions for causing the processing device to:

measure a delay between the notification and an increase in the user's glucose levels as indicated by the determined changes, wherein computing the physiological response estimate is further based on the measured delay.

\* \* \* \* \*